United States Patent
Maruyama et al.

(10) Patent No.: US 11,021,628 B2
(45) Date of Patent: Jun. 1, 2021

(54) COATING COMPOSITION CONTAINING METHYL CELLULOSE, METHOD FOR PRODUCING THE SAME, AND SOLID PREPARATION

(71) Applicant: Shin-Etsu Chemical Co., Ltd., Tokyo (JP)

(72) Inventors: Naosuke Maruyama, Niigata-ken (JP); Takuya Yokosawa, Niigata-ken (JP); Akira Kitamura, Niigata-ken (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/450,511

(22) Filed: Mar. 6, 2017

(65) Prior Publication Data
US 2017/0260414 A1    Sep. 14, 2017

(30) Foreign Application Priority Data

Mar. 9, 2016  (JP) .............................. JP2016-045745

(51) Int. Cl.
*C09D 101/00* (2006.01)
*C09D 101/28* (2006.01)
(Continued)

(52) U.S. Cl.
CPC .......... *C09D 101/28* (2013.01); *A61K 9/5047* (2013.01); *C08B 11/02* (2013.01); *C09D 7/69* (2018.01)

(58) Field of Classification Search
CPC combination set(s) only.
See application file for complete search history.

(56) References Cited

U.S. PATENT DOCUMENTS 2,716,072 A * 8/1955 Hanson ..................... C08L 1/28
                                                            106/189.1
5,324,445 A * 6/1994 Langley ................. A01N 25/10
                                                            510/321
(Continued)

FOREIGN PATENT DOCUMENTS

EP    2 754 438 A1    7/2014
EP    2 754 673 A1    7/2014
(Continued)

OTHER PUBLICATIONS

Extended European Search Report for European Application No. 17158252.1 dated Jun. 21, 2017, 4 pages.
(Continued)

*Primary Examiner* — Stefanie J Cohen
(74) *Attorney, Agent, or Firm* — Rimon, P.C.

(57) ABSTRACT

Regarding coating of fine particles or the like, provided are a coating composition containing methyl cellulose having small adhesiveness, resistance to generation of lumps, ability to form uniform coating, and ability to form a coating composition easily with water of normal temperature; a method for producing the coating composition; and a solid preparation. More specifically provided are a coating composition including methyl cellulose having such a viscosity that a viscosity at 20° C. of a 2% by weight aqueous solution of the methyl cellulose is 1 to 15 mPa·s and having such a dissolution start temperature that a dissolution start temperature of a 12% by weight aqueous liquid of the methyl cellulose is 10 to 25° C. and a solvent; a solid preparation obtained by coating of the coating composition; and the like.

9 Claims, 1 Drawing Sheet

(51) Int. Cl.
*C09D 7/40* (2018.01)
*A61K 9/50* (2006.01)
*C08B 11/02* (2006.01)

(56) References Cited

U.S. PATENT DOCUMENTS

| | | | |
|---|---|---|---|
| 6,235,893 B1* | 5/2001 | Reibert | C08B 11/02 |
| | | | 264/140 |
| 2011/0077391 A1* | 3/2011 | Hayakawa | C08B 11/193 |
| | | | 536/91 |
| 2013/0236512 A1* | 9/2013 | Adden | C08B 11/193 |
| | | | 424/400 |
| 2014/0199406 A1* | 7/2014 | Yokosawa | A61K 9/5042 |
| | | | 424/494 |

FOREIGN PATENT DOCUMENTS

| | | | |
|---|---|---|---|
| EP | 3 031 828 A1 | | 6/2016 |
| JP | 60-13719 A | | 1/1985 |
| JP | 62-25101 A | | 2/1987 |
| JP | 2001-192344 A | | 7/2001 |
| JP | 2014-133722 A | | 7/2014 |
| WO | WO02/03967 | * | 1/2002 |
| WO | WO 2014/168914 A1 | | 10/2011 |
| WO | WO 2012/051034 A1 | | 4/2012 |
| WO | WO 2015/009796 A1 | | 1/2015 |

OTHER PUBLICATIONS

Communication of a Notice of Opposition for European Application No. 17158252.1 dated Mar. 22, 2019. 16 pages.
Analysis of Methylcellulose MC-1 Disclosed in WO 2015/009796 A1 (submitted with Opposition dated Mar. 18, 2019—Document D2) 3 pages.
Properties of Methylcellulose (B) Disclosed in WO 2014/168914, Having a Steady-Shear-Flow viscosity $\eta(5°\ C., 10\ s^{-1}, 2\ wt.\%\ MC)$ of 4 mPa·s (submitted with Opposition dated Mar. 18, 2019—Document D4) 3 pages.
Methocel™ Premium Cellulose Ethers (Technical Bulletin) (submitted with Opposition dated Mar. 18, 2019—Document D7) 2 pages.
Particle Size Analysis of Methocel™ K250M Cellulose Ether (submitted with Onposition dated Mar. 18, 2019—Document D6) 1 page.
*Viscosity Determination*, Section 2.53, pp. 67-69, Japanese Pharmacopoeia, Sixteenth Edition (2011), 21 pages.
Kokubo, Hiroyasu et al.; "Application of Extremely Low Viscosity Methylcellulose (MC) for Pellet Film Coating"; Chem. Pharm, Bull. 46(11) 1803-1806 (1998).

* cited by examiner

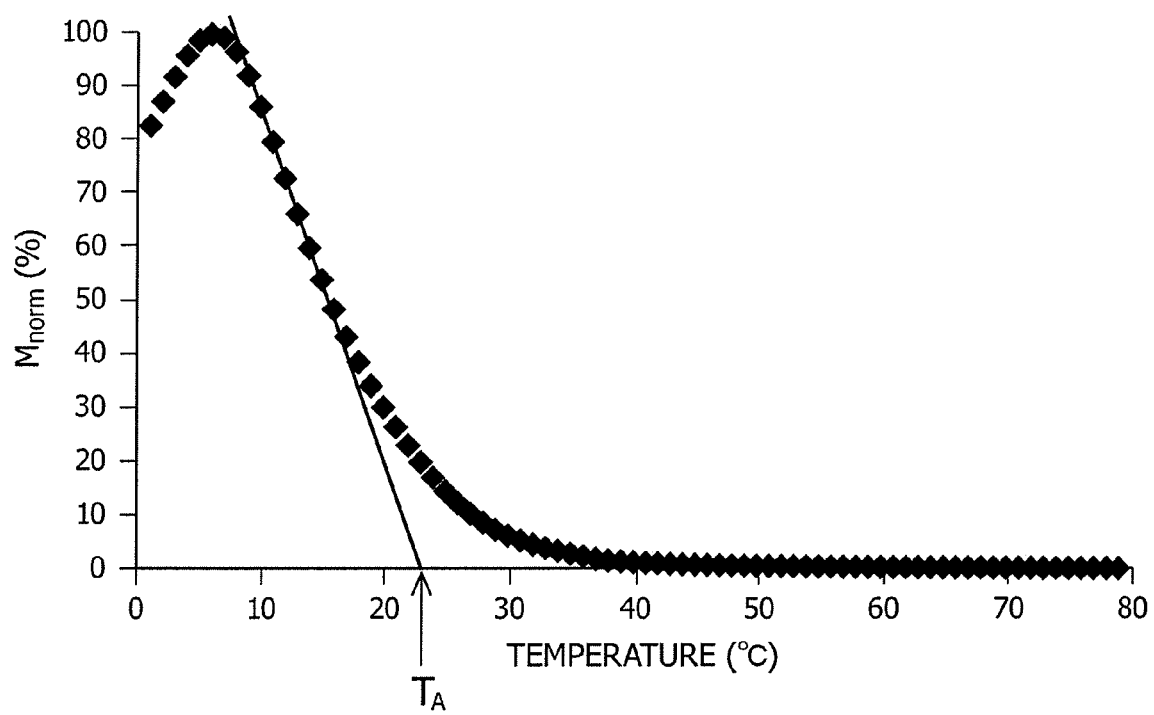

US 11,021,628 B2

COATING COMPOSITION CONTAINING METHYL CELLULOSE, METHOD FOR PRODUCING THE SAME, AND SOLID PREPARATION

FIELD

The present invention relates to a coating composition containing methyl cellulose and being used as a coating agent which masks unpleasant tastes such as bitterness of a solid preparation and has excellent dissolution properties of a drug; a method for producing the composition; and a solid preparation.

BACKGROUND

In recent years, there is a demand for the development of orally disintegrating tablets which can be easily taken without water by patients having low swallowing ability such as elderly and child patients. When an orally disintegrating tablet contains a drug with unpleasant tastes such as bitterness, a patient may have difficulty in taking the tablet because of the dissolution of the drug in the oral cavity. In order to suppress the dissolution of a drug in the oral cavity, for example, a method of coating the tablet with a water-insoluble coating base material has been considered. However, such a coating can also suppress the dissolution of a drug in the alimentary canal, so that insufficient pharmaceutical effect can be achieved.

On the other hand, when a water-soluble polymer such as hypromellose and hydroxypropyl cellulose is used for coating, a high dissolution rate thereof in the oral cavity due to the water-solubility thereof results in insufficient masking of unpleasant tastes such as bitterness.

Of these water-soluble polymers, methyl cellulose is known to have a high bitterness masking effect and low slimy feeling in the oral cavity (JP 60-13719A). A coating prepared by using a mixed base material of a pH-dependent acrylic polymer and methyl cellulose as a water-soluble polymer is also known to have an improved effect of masking unpleasant tastes such as bitterness (JP 2001-192344A). Another coating prepared by using a mixed base material of a cellulose-type enteric base material and a water-soluble cellulose ether is also disclosed (JP 2014-133722A). Methyl cellulose is known to bring smaller adhesiveness than that of hypromellose and generate fewer lumps when applied to granule coating (Chem. Pharm. Bull., 46 (11) 1803-1806 (1998)).

SUMMARY

The methyl cellulose disclosed in JP 60-13719A has insufficient masking of bitterness when applied to fine particles having small particle sizes. When the pH-dependent acrylic polymer disclosed in JP 2001-192344A is used, the dissolution properties of a drug may vary with changes of pH in the stomach due to, for example, achlorhydria. In addition, the acrylic polymer, which has high tackiness, is apt to generate lumps when applied to fine particle coating, so that it is difficult to provide a uniform coating. The cellulose-type enteric base material disclosed in JP 2014-133722A is also a pH-dependent polymer and has substantially the same problem as that of the acrylic polymer. The application of the methyl cellulose disclosed in Chem. Pharm. Bull., 46 (11) 1803-1806 (1998) to granule coating is effective when the methyl cellulose is applied to pellets having comparatively large particle sizes. However, when applied to fine particles having an average particle size of 300 μm or less, the methyl cellulose is still apt to generate lumps during coating.

Drug particles contained by an orally disintegrating tablet are required to be fine particles from the standpoint of bioavailability. However, coating of fine particles is apt to generate lumps due to larger surface areas thereof during coating as compared with conventional tablet coating and the like, so that it is difficult to provide a uniform coating. Thus, there is a demand for the development of a coating agent having low adhesiveness.

In the preparation of a solution of a conventional water-soluble polymer such as hypromellose, hydroxypropyl cellulose and methyl cellulose, addition of a powder directly to water of normal temperature generates agglomerates (mamako in Japanese), and it takes a long time to dissolve the agglomerates. Hence, after a powder is dispersed in hot water, the dispersion is required to be cooled and dissolved. Such operations complicate the preparation of a coating composition. Thus, there is a demand for the development of a coating composition which can be simply prepared with water of normal temperature.

An object of the present invention is, with respect to coating of fine particles and others, to provide a coating composition containing methyl cellulose having small adhesiveness, resistance to generation of lumps during coating of fine particles or the like, ability to form a uniform coating, and ability to prepare a coating composition easily with water of normal temperature; a method for producing the coating composition; and a solid preparation.

As a result of intensive studies for solving the above problems, the present inventors have found that a coating composition containing methyl cellulose having small adhesiveness, resistance to generation of lumps, ability to form a uniform coating, and ability to prepare a coating composition easily with water of normal temperature is provided; and a solid preparation coated with the coating composition has an excellent masking effect of bitterness and excellent dissolution properties, and have completed the present invention.

In an aspect of the present invention, provided is a coating composition comprising methyl cellulose having such a viscosity that a viscosity at 20° C. of a 2% by weight aqueous solution of the methyl cellulose is 1 to 15 mPa·s and having such a dissolution start temperature that a dissolution start temperature of a 12% by weight aqueous dispersion of the methyl cellulose is 10 to 25° C.; and a solvent.

In another aspect of the present invention, provided is a solid preparation obtained by coating of the coating composition.

In still another aspect of the present invention, provided is a method for producing a coating composition, comprising the steps of: mixing a cellulose pulp and a first alkali metal hydroxide solution with stirring to obtain alkali cellulose; reacting the alkali cellulose with a methylating agent to obtain a first reaction mixture; mixing the first reaction mixture and a second alkali metal hydroxide solution with stirring and without further addition of any methylating agent to obtain a second reaction mixture; isolating methyl cellulose from the second reaction mixture; depolymerizing the methyl cellulose to obtain low-polymerization-degree methyl cellulose; and dissolving the low-polymerization-degree methyl cellulose in a solvent; wherein a ratio of a weight of a first alkali metal hydroxide in the first alkali metal hydroxide solution to a total weight of the first alkali metal hydroxide in the first alkali metal hydroxide solution and a second alkali metal hydroxide in the second alkali metal hydroxide solution is 50 to 86%.

According to the present invention, with respect to coating of a solid preparation, especially to coating of fine particles, a coating composition containing methyl cellulose having small adhesiveness, resistance to generation of lumps, ability to form a uniform coating, and ability to prepare a coating composition easily with water of normal temperature is provided. In addition, a solid preparation obtained by coating of the coating composition exhibits an excellent masking effect of bitterness and excellent dissolution properties.

BRIEF DESCRIPTION OF THE DRAWINGS

FIGURE exhibits a graph showing a method of determining the dissolution start temperature of methyl cellulose.

DETAILED DESCRIPTION

The present invention will now be described in detail with reference to preferred embodiments of the present invention. The invention is not intended to be limited to the embodiments.

A 2% by weight aqueous solution of methyl cellulose has a viscosity at 20° C. of 1 to 15 mPa·s, preferably 3 to 12 mPa·s, more preferably 3 to 8 mPa·s. When the viscosity is less than 1 mPa·s, a resulting coating has low film strength and the masking effect is reduced. When the viscosity is more than 15 mPa·s, the viscosity is too high to increase the concentration of such methyl cellulose in a coating composition, thereby lowering the productivity.

The viscosity at 20° C. of a 2% by weight aqueous solution of methyl cellulose can be calculated from the value determined by the viscosity determination of methyl cellulose in accordance with the Japanese Pharmacopoeia Sixteenth Edition.

A 12% by weight aqueous dispersion of the methyl cellulose has a dissolution start temperature of 10 to 25° C., preferably 15 to 24° C., more preferably 18 to 23° C. When the dissolution start temperature is less than 10° C., such methyl cellulose is not dissolved in water of normal temperature, and thus is required to be cooled during preparation of a coating composition. When a coating composition is prepared without cooling, the film formability deteriorates. When the dissolution start temperature is more than 25° C., agglomerates (mamako in Japanese) are formed during preparation of a solution, and it takes a long time to dissolve such methyl cellulose. The methyl cellulose has a lower dissolution start temperature than that of conventional methyl cellulose. Thus, even when water of normal temperature is used to prepare a coating composition, a powder can be immediately moistened and then dissolved without formation of agglomerates.

When a coating composition comprises methyl cellulose having the above dissolution start temperature, the coating composition has a high effect of suppressing the dissolution of a drug from a coated solid preparation and has a high effect of masking unpleasant tastes such as bitterness because the methyl cellulose is not dissolved at about 37° C., which is the normal body temperature.

The dissolution start temperature can be determined by plotting the generated torque values against temperatures as methyl cellulose dispersed in hot water is cooled. The dissolution start temperature can be determined by using a rheometer such as MCR301 manufactured by Anton Paar.

The dissolution start temperature of methyl cellulose is specifically determined by the method comprising the steps of: adjusting the temperature of a CC27 measurement cup (CC27/T200/AL, a cylindrical aluminum container having a diameter of 29 mm and a height of 68 mm) placed in the sample-measuring-section of a rheometer to 80° C.; accurately weighing 4.8 g of the methyl cellulose on pharmaceutical paper; adding the methyl cellulose and 35.2 g of hot water (98° C.) into the measurement cup taken out of the rheometer to make a total weight of 40.0 g; thoroughly mixing the resulting mixture with stirring by using a blade type measurement jig (ST24-2D/2V/2V-30) to allow the methyl cellulose to be completely dispersed to obtain a dispersion having a methyl cellulose concentration of 12% by weight; returning the measurement cup and the blade type measurement jig into the sample-measuring section of the rheometer; stirring the dispersion at 400 rpm for 5 minutes while controlled at 80° C.; and then stirring the dispersion at 400 rpm while cooling the temperature of the sample-measuring-section to 1° C. at the rate of 1° C./min with a Peltier temperature controller. The torque values are recorded at a point per minute from 80° C. to 1° C., and the increase of torque values is shown as a function of temperature. The obtained data are normalized in accordance with the following equation.

$$M_{norm}(\%)=\{(M-M_i)/(M_{max}-M_i)\}\times 100$$

In the equation, $M_{norm}$ represents a normalized torque value; M represents a torque value measured at each temperature; $M_i$ represents a torque value at the initial temperature (80° C.); and $M_{max}$ represents the maximum torque value of the obtained torque values. A graph is prepared where the horizontal axis represents temperature and the vertical axis represents $M_{norm}$, and a linear regression is prepared from five or more points in a temperature range of 5° C. or more. The intersection of a linear regression having a maximum slope and a sufficient coefficient of correlation ($R^2=0.99$ or more) and the X axis (temperature axis) is defined as the dissolution start temperature. FIGURE is a graph showing the method of determining the dissolution start temperature of methyl cellulose. In this example, the dissolution start temperature is $T_A$.

A 15% by weight aqueous solution of the methyl cellulose has a gelation temperature of preferably 13 to 25° C., more preferably 15 to 24° C., even more preferably 18 to 23° C. from the standpoint of the effect of suppressing tackiness due to gelation. The methyl cellulose has a lower gelation temperature than that of conventional methyl cellulose.

A coating composition is sprayed and concurrently dried by hot air to form a film during usual coating. Thus, a coating composition containing the methyl cellulose having a lower gelation temperature than that of conventional methyl cellulose rapidly undergoes gelation by hot air during coating, so that the tackiness of the coating solution is reduced. This reduction can lower the adhesiveness between particles to suppress the generation of lumps.

The discharge temperature or the material temperature during typical aqueous coating is 40 to 50° C. When the methyl cellulose has a gelation temperature of less than the discharge temperature or the material temperature, the methyl cellulose is supposed to immediately undergo gelation upon spraying of a coating composition to granules or the like, so that the tackiness of the solution is reduced to suppress the generation of lumps. In particular, this effect is remarkable for fine particles such as particles having an average particle size of 300 μm or less, which are apt to generate lumps as compared with tablets and the like. Thus, this coating composition is particularly suitable to the coating of the solid preparation of fine particles.

The gelation temperature is evaluated by using the relation between a storage elastic modulus G'(5→90° C.) and a loss elastic modulus G". Generally, the loss elastic modulus means a viscous factor of a solution, or a factor of such characteristics that a fluid is deformed by fluid movement to generate resistance.

The gelation temperature of a 15% by weight aqueous solution of methyl cellulose can be determined with a rheometer such as MCR301 manufactured by Anton Paar.

The temperature of the sample-measurement-section of a rheometer is adjusted to 5° C. in advance, and the 15% by weight aqueous solution of methyl cellulose is placed in the sample-measurement-section. Parallel plates having a diameter of 50 mmϕ (PP-50) are used as the measurement jigs to select the measurement gap of 0.5 mm. The outer periphery of the measurement jigs is covered with silicone oil, and the sample is allowed to stand at 5° C. for 5 minutes. Then, a distortion with a frequency of 1 Hz and an amplitude of 1% is applied to start the measurement. The temperature of the sample-measurement-section is increased to 90° C. at 2° C./min with a Peltier temperature controller. The data are collected at two points per minute.

The storage elastic modulus G'(5→90° C.) and the loss elastic modulus G" determined by the measurement are variable as the temperature of the measurement system increases. The temperature at which the storage elastic modulus G'(5→90° C.) becomes equal to the loss elastic modulus G", or the temperature at which G"/G' is 1 is regarded as the gelation temperature.

The methyl cellulose preferably has a degree of substitution (DS) of methoxy group per anhydroglucose unit of 1.61 to 2.03, more preferably 1.74 to 2.03. When the DS is less than 1.61, the methyl cellulose may have a lower solubility in water. When the DS is more than 2.03, larger amounts of a methylating agent and an alkali metal hydroxide are required so that an economic disadvantage may be brought. The degree of substitution of methoxy group can be determined by the determination method for methyl cellulose in accordance with the Japanese Pharmacopoeia Sixteenth Edition. Here, the DS is degree of substitution and represents an average number of hydroxy groups substituted by alkyl groups (methyl groups in this case) per anhydroglucose unit of cellulose.

Next, the method for producing the methyl cellulose will be described.

Generally, methyl cellulose can be produced by the method comprising the steps of: bringing a starting material cellulose pulp into contact with an alkali metal hydroxide solution to obtain alkali cellulose and then reacting the alkali cellulose with a methylating agent. In the present invention, an alkali metal hydroxide solution is blended in two or more steps, and a methylating agent is added in one step so that methyl cellulose having a lower dissolution start temperature than that of conventional methyl cellulose can be produced and can provide a coating composition by using water of normal temperature without need of dispersing in hot water and cooling. In addition, the adhesiveness during coating is reduced to suppress the generation of lumps.

More specifically, the intended methyl cellulose can be produced by the method comprising the steps of: mixing a cellulose pulp and a first alkali metal hydroxide solution with stirring to obtain alkali cellulose; reacting the alkali cellulose with a methylating agent to obtain a first reaction mixture; mixing the first reaction mixture and a second alkali metal hydroxide solution with stirring and without further addition of any methylating agent to obtain a second reaction mixture; and isolating methyl cellulose from the second reaction mixture, wherein a ratio of the weight of a first alkali metal hydroxide in the first alkali metal hydroxide solution to the total weight of the first alkali metal hydroxide in the first alkali metal hydroxide solution and a second alkali metal hydroxide in the second alkali metal hydroxide solution is 50 to 86%.

The cellulose pulp is exemplified by wood pulp and linter pulp, and is used as a raw material for the production of a typical cellulose ether. The intrinsic viscosity as an index of the polymerization degree of a cellulose pulp can be appropriately selected depending on the viscosity of an aqueous solution of an intended cellulose ether, and is preferably 1,000 to 2,200 ml/g, more preferably 1,300 to 2,000 ml/g at 25° C. The intrinsic viscosity of a cellulose pulp can be determined by a method in accordance with method A in Japanese Industrial Standards (JIS) P8215.

The cellulose pulp contains cellulose and water. In the present specification, the amount of "the cellulose in a cellulose pulp" can be calculated from the dry matter content determined in accordance with Pulps—Determination of dry matter content in JIS P8203: 1998. The dry matter content is determined by the method comprising the steps of: drying a sample at 105±2° C. until the weight of the sample reaches a constant value; and calculating a weight ratio (%) of the dried sample to the sample prior to drying.

The cellulose pulp is preferably a cellulose pulp powder prepared by pulverization with a pulverizer. The pulp pulverizer may be any pulverizer which can make a cellulose pulp into a powder, and may be a pulverizer such as a knife mill, a cutting mill, a hammer mill, a ball mill and a vertical roller mill. The cellulose pulp powder preferably has a weight average particle size $D_{50}$ of 30 to 400 μm. The weight average particle size $D_{50}$ of cellulose pulp powder is determined by the method comprising the steps of: installing a plurality of test sieves having various mesh sizes in accordance with JIS Z8801 in a Ro-Tap® sieve shaker; placing a cellulose pulp powder in the uppermost sieve; vibrating or tapping the cellulose pulp powder for sieving; and then determining the weight on each sieve and the weight under the sieves to obtain the weight distribution and the average particle size at an integrated value of 50% as the weight average particle size $D_{50}$.

Next, the step of mixing a cellulose pulp and a first alkali metal hydroxide solution with stirring to obtain alkali cellulose will be described.

The alkali metal hydroxide solution is blended in two stages as a first alkali metal hydroxide solution and a second alkali metal hydroxide solution. The alkali metal hydroxide solution is not particularly limited, and is exemplified by a solution of sodium hydroxide or potassium hydroxide. An aqueous sodium hydroxide solution is preferred from the standpoint of economy. A kind of the first alkali metal hydroxide in the first alkali metal hydroxide solution is preferably the same as that of the second alkali metal hydroxide in the second alkali metal hydroxide solution. For example, each of the first and second alkali metal hydroxides is sodium hydroxide. However, the first and second alkali metal hydroxides can be a combination of different kinds of hydroxides. For example, sodium hydroxide can be used as the first alkali metal hydroxide, while potassium hydroxide can be used as the second alkali metal hydroxide.

The blending of the alkali metal hydroxide solution is preferably adding of the alkali metal hydroxide solution to a cellulose pulp. Examples of the addition include direct dropping of the alkali metal hydroxide solution, or spraying of the alkali metal hydroxide solution. The spraying is preferable from the standpoint of good uniformity of the resulting alkali cellulose.

The concentration of the alkali metal hydroxide in the alkali metal hydroxide solution is preferably 10 to 60% by weight, more preferably 30 to 50% by weight from the standpoint of etherification reaction efficiency and handleability. The first alkali metal hydroxide and the second alkali metal hydroxide preferably have the same concentrations, but can have different concentrations.

The step of mixing a cellulose pulp and an alkali metal hydroxide solution with stirring is preferably carried out in a reactor having a stirring structure inside. The reactor is preferably equipped with a measurement device such as a device capable of measuring the inside temperature.

Before mixing the first alkali metal hydroxide solution and the cellulose pulp with stirring, it is preferred that oxygen in the reactor be removed by a vacuum pump or the like and be replaced with an inert gas, preferably nitrogen, to suppress depolymerization which can proceed in the presence of an alkali metal hydroxide and oxygen.

Regarding the amount of the first alkali metal hydroxide solution, a molar ratio of the first alkali metal hydroxide to the cellulose in the cellulose pulp (first alkali metal hydroxide/cellulose) is preferably 2.0 to 4.0, more preferably 2.7 to 3.5. When the molar ratio of the first alkali metal hydroxide to the cellulose is more than 4.0, methyl cellulose having a low dissolution start temperature may not be produced.

The ratio of the weight of the first alkali metal hydroxide in the first alkali metal hydroxide solution to the total weight of the first alkali metal hydroxide in the first alkali metal hydroxide solution and the second alkali metal hydroxide in the second alkali metal hydroxide solution is 50 to 86%, preferably 65 to 80%, more preferably 65 to 75%. When the ratio of the weight of the first alkali metal hydroxide to the total weight of the first and second alkali metal hydroxides is less than 50%, cooling is required during preparation of a coating composition due to an excessively low dissolution start temperature. When the ratio is more than 86%, methyl cellulose having a low dissolution start temperature cannot be produced.

The inside temperature of the reactor during blending of the cellulose pulp with the first alkali metal hydroxide, preferably during addition of the first alkali metal hydroxide solution to the cellulose pulp, is preferably 10 to 80° C., more preferably 30 to 70° C. from the standpoint of uniform alkali cellulose.

The blending rate of the first alkali metal hydroxide in the first alkali metal hydroxide solution means the molar amount of the first alkali metal hydroxide added per unit time relative to 1 mol of the cellulose in the cellulose pulp, and is preferably 1.5 to 48 [mol/mol·hr], more preferably 4.8 to 18.6 [mol/mol·hr], even more preferably 8 to 15 [mol/mol·hr] from the standpoint of uniform mixing of the first alkali metal hydroxide solution in the system. After the addition of the first alkali metal hydroxide solution, the mixing can be continued with stirring for another 5 to 30 minutes to make the alkali cellulose more uniform.

To suppress local generation of heat in the reactor, an organic solvent not affecting the methylation, such as dimethyl ether, can be added to the system before, during, or after the addition of the first alkali metal hydroxide solution.

Next, the prepared alkali cellulose is reacted with a methylating agent to obtain a first reaction mixture.

Examples of the methylating agent include methyl chloride, dimethyl sulfate and methyl iodide. The methyl chloride is preferred from the standpoint of the solubility of the resulting methylcellulose in water and economy.

The inside temperature of the reactor during the reaction with the methylating agent is preferably 40 to 90° C., more preferably 50 to 80° C. from the standpoint of reaction control.

Regarding the molar amount of the methylating agent, a molar ratio of the methylating agent to the total amount of the first and second alkali metal hydroxides (methylating agent/total of alkali metal hydroxides) is preferably 0.8 to 1.5, more preferably 1.0 to 1.3. When the molar ratio of the methylating agent to the total of alkali metal hydroxides is less than 0.8, an intended number of methyl groups may not be added through substitution. When the molar ratio is more than 1.5, an excessive amount of the methylating agent may lead to an economic disadvantage.

As for the blending of the methylating agent, the methylating agent is preferably added to the alkali cellulose. The period of time for adding the methylating agent is preferably 30 to 120 minutes, more preferably 40 to 90 minutes from the standpoint of reaction control and productivity.

The methyl cellulose in the first reaction mixture has a degree of substitution (DS) of methyl group of preferably 0.75 to 1.68, more preferably 0.81 to 1.68, even more preferably 0.99 to 1.37 from the standpoint of obtaining an intended dissolution start temperature.

Subsequently, the first reaction mixture is mixed with a second alkali metal hydroxide solution with stirring and without further addition of any methylating agent to obtain a second reaction mixture. The first reaction mixture to be mixed with the second alkali metal hydroxide solution may be the reaction mixture in which some or all of the methylating agent has been added.

The timing of blending the first reaction mixture with the second alkali metal hydroxide solution, that is, the timing of starting of the blending of the second alkali metal hydroxide solution, is preferably after 80% by weight or more of the total amount of the methylating agent to be blended has been added, more preferably after the completion of the addition of the methylating agent. When the timing of starting the addition of the second alkali metal hydroxide solution is before 80% by weight of the total amount of the methylating agent to be blended has been added, methyl cellulose having a low dissolution start temperature may not be produced.

Regarding the amount of the second alkali metal hydroxide in the second alkali metal hydroxide solution, a molar ratio of the second alkali metal hydroxide in the second alkali metal hydroxide solution to the cellulose in the cellulose pulp (second alkali metal hydroxide/cellulose) is preferably 0.65 to 2.0, more preferably 0.88 to 1.48. When the molar ratio of the second alkali metal hydroxide to the cellulose is less than 0.65, methyl cellulose having a low dissolution start temperature may not be produced.

The inside temperature of the reactor at the start of the blending of the second alkali metal hydroxide solution with the first reaction mixture, preferably at the start of the addition of the second alkali metal hydroxide solution to the first reaction mixture, is preferably 65 to 90° C., more preferably 75 to 85° C. When the inside temperature of the reactor at the start of the addition of the second alkali metal hydroxide solution is less than 65° C., methyl cellulose having a low dissolution start temperature may not be produced. When the inside temperature of the reactor at the start of the addition is more than 90° C., heat generation due to mercerization by the alkali metal hydroxide or the exothermic reaction of methylation may not be controlled. The inside temperature of the reactor at the completion of the blending of the second alkali metal hydroxide solution is preferably 80° C. to 100° C., more preferably 85 to 95° C. from the standpoint of production of methyl cellulose having a low dissolution start temperature. The temperature at the start of the addition is lower than that at the completion of the addition, and the temperature difference therebetween is preferably 3 to 20° C., more preferably 4 to 15° C.

The blending rate of the second alkali metal hydroxide in the second alkali metal hydroxide solution means the molar amount of the second alkali metal hydroxide to be blended with the first reaction mixture per unit time relative to 1 mol of the cellulose in the cellulose pulp, and is preferably 0.5 to 9.6 [mol/mol·hr], more preferably 1.0 to 6.5 [mol/mol·hr], even more preferably 1.0 to 3.5 [mol/mol·hr]. When the blending rate of the second alkali metal hydroxide is less than 0.5 [mol/mol·hr], the period of time for blending the second alkali metal hydroxide becomes long so that the reaction time may be extended. When the blending rate of the second alkali metal hydroxide is more than 9.6 [mol/mol·hr], methyl cellulose having a low dissolution start temperature may not be produced.

In the step of blending the second alkali metal hydroxide solution with the first reaction mixture, it is preferred that the second alkali metal hydroxide solution be blended while the inside temperature of the reactor be increased at a constant increase rate from the start to the completion of the blending of the second alkali metal hydroxide solution from the standpoint of production of methyl cellulose having a low dissolution start temperature. The temperature increase rate is preferably 3.0 to 50° C./hr, more preferably 8.0 to 45° C./hr, even more preferably 8.0 to 30° C./hr.

Generally, alkali cellulose prepared by mixing a cellulose pulp with an alkali metal hydroxide solution is etherified with a methylating agent to produce methyl cellulose. In this case, the methylating agent in the reaction system is gradually consumed as the etherification proceeds. When the inside temperature of the reactor is constant, the reaction rate of the etherification gradually decreases as the methylating agent is consumed in the reaction system. On this account, by blending the second alkali metal hydroxide solution while increasing the inside temperature of the reactor at a constant rate, the decrease of the reaction rate of the etherification caused by the consumption of the methylating agent in the reaction system is suppressed, and the reaction rate of the etherification associated with the blending of the second alkali metal hydroxide solution is relatively increased. As a result, methyl cellulose having a low dissolution start temperature can be produced.

After the blending of the second alkali metal hydroxide solution, the mixing with stirring is preferably continued to complete the etherification.

The inside temperature of the reactor during the mixing with stirring after the blending of the second alkali metal hydroxide solution is preferably 80 to 120° C., more preferably 85 to 100° C. from the standpoint of reaction controllability. To complete the reaction, the mixture is preferably heated after the blending of the second alkali metal hydroxide solution.

The period of time for the mixing with stirring after the blending of the second alkali metal hydroxide solution is preferably 10 to 60 minutes, more preferably 20 to 40 minutes from the standpoint of productivity.

Methyl cellulose may be isolated from the obtained second reaction mixture in the same purification method as in the usual purification of crude methyl cellulose. The purification method and the purification device are not particularly limited. The purification can be carried out preferably with water, more preferably with hot water (preferably of 60 to 100° C.). More specifically, the purification (i.e. isolation) may be carried out by the method comprising the steps of: mixing the second reaction mixture with water in a stirring container to allow the salts generated as by-products to be dissolved; and subjecting the suspension discharged from the stirring container to a separation operation to remove the salts.

After the purification, the isolated product may be optionally dried. The drying method and the dryer are not particularly limited. The temperature of the methyl cellulose during drying is preferably 40 to 80° C.

The produced methyl cellulose may be optionally subjected to pulverization with a common pulverizer such as a ball mill, a roller mill and an impact grinder, followed by classification through a sieve to adjust the particle size.

The viscosity at 20° C. of a 2% by weight aqueous solution of the methyl cellulose before the depolymerization reaction described later is not particularly limited, and is preferably more than 20 mPa·s, more preferably 50 to 150,000 mPa·s. When the viscosity at 20° C. of the 2% by weight aqueous solution of methyl cellulose is 600 mPa·s or more, it may be determined by using a single cylinder-type rotational viscometer in accordance with "Viscosity measurement by rotational viscometer" in Viscosity Determination of General Tests described in the Japanese Pharmacopoeia Sixteenth Edition. When it is less than 600 mPa·s, it may be determined by using an Ubbelohde-type viscometer in accordance with "Viscosity measurement by capillary tube viscometer" in Viscosity Determination of General Tests described in the Japanese Pharmacopoeia Sixteenth Edition.

When the produced methyl cellulose is used as it is and as a coating composition, the composition has an excessively high viscosity. Accordingly, the viscosity of the methyl cellulose is controlled by subjecting the methyl cellulose to a depolymerization reaction to such an extent that a 2% by weight aqueous solution of the methyl cellulose has a viscosity at 20° C. of 1 to 15 mPa·s, preferably 3 to 10 mPa·s, for example, by a method in accordance with JP 62-25101A.

The depolymerization method includes depolymerization by hydrolysis with an acid catalyst and depolymerization by oxidative decomposition with an oxidizing agent, and is preferably depolymerization by hydrolysis with an acid catalyst from the standpoint of storage stability.

Examples of the acid to be used for the depolymerization by hydrolysis with an acid catalyst preferably include inorganic acids such as hydrochloric acid, sulfuric acid, nitric acid and phosphoric acid. The acid may be used singly or in combination of two or more. The addition of an acid to a system includes addition in a gas state or in a solution state, and is preferably addition in a solution state. The weight of an acid is preferably 0.1 to 3.0% by weight, more preferably 0.15 to 1.5% by weight relative to the weight of methyl cellulose.

The inside temperature of the reactor during the depolymerization is not particularly limited, and is preferably 50 to 130° C., more preferably 60 to 110° C., even more preferably 60 to 90° C. The depolymerization time is preferably selected according to the viscosity value at 20° C. of a 2% by weight aqueous solution of each methyl cellulose before and after the depolymerization, as well as depolymerization conditions.

Next, the coating composition will be described.

The coating composition may comprise water as a solvent. The coating composition may comprise a mixed solvent of water and an alcohol such as ethanol and methanol other.

In the coating composition, the concentration of the methyl cellulose is preferably 3 to 15% by weight, more preferably 5 to 10% by weight from the standpoint of coating time and viscosity.

The coating composition may comprise an additive such as a plasticizer, a pigment, a coloring agent, talc, an anti-tack agent, an anti-foaming agent, and a flavoring agent.

Examples of the plasticizer include polyethylene glycol, glycerol, propylene glycol, triacetin and triethyl citrate. Polyethylene glycol and glycerol are preferred from the standpoint of excellent compatibility with methyl cellulose. An amount of the plasticizer is generally increased in a composition containing a larger amount of a pigment. An amount of the plasticizer is typically preferably in a range of 3 to 50% by weight relative to an amount of the methyl cellulose.

Examples of the pigment include titanium oxide, aluminum lake and food dyes. The amount of the pigment varies with a purpose of light shielding or coloring, and is preferably in a range of 0.1 to 30% by weight relative to an amount of the methyl cellulose.

Examples of the anti-tack agent include solid polyethylene glycol, Aerosil (silicon dioxide) and titanium dioxide.

Examples of the anti-foaming agent include silicone antifoaming agents such as KM-72 (manufactured by Shin-Etsu Chemical Co., Ltd.), polyoxyethylene polyoxypropylene glycol anti-foaming agents such as Pluronic F68 (manufactured by Asahi Denka Kogyo K.K.), and sorbitan sesquioleate.

Examples of the flavoring agent include spearmint and menthol.

The amounts of the coloring agent, the talc, the anti-tack agent, the anti-foaming agent and the flavoring agent are the same as the amounts typically used in a coating composition.

The coating composition in the present invention may further comprise an additional coating base material to such an extent as not to impair the advantageous effects of the present invention. Examples of the additional coating base material include water-soluble vinyl derivatives such as polyvinylpyrrolidone and polyvinyl alcohol; acrylic acid copolymers such as methacrylic acid copolymer LD and ethyl acrylate/methyl methacrylate copolymer dispersion liquids; and cellulose derivatives such as ethyl cellulose, hydroxypropyl cellulose, hydroxypropyl methyl cellulose, hydroxypropyl methyl cellulose phthalate and hydroxypropyl methyl cellulose acetate succinate.

The method for preparing the coating composition may be a method of adding the methyl cellulose to water of normal temperature (15 to 25° C.) described in the Japanese Pharmacopoeia or to a mixed solvent of water and an alcohol such as ethanol and methanol; or a method of adding water of normal temperature or a mixed solvent of water and an alcohol such as ethanol and methanol to the methyl cellulose.

An optional additive such as a plasticizer may be further added to the aqueous solution or mixed solution of the methyl cellulose to prepare a coating composition.

Next, the solid preparation will be described.

The solid preparation is produced by coating a drug substance or a core particle containing a drug with the coating composition. Examples of the solid preparation include tablets, granules, fine granules and capsules, and also include orally rapidly disintegrating tablets.

The drug may be any drug which can be orally administered. The solid preparation is particularly effective on a drug exhibiting unpleasant tastes such as bitterness and astringent taste. Examples of the drug exhibiting such an unpleasant taste include acetaminophen, aspirin, ibuprofen, ethenzamide, phenacetin, mefenamic acid, antipyrine, phenylbutazone, sulpyrine, diclofenac sodium, ketoprofen, naproxen, loxoprofen sodium, etodolac, epirizole, tiaramide hydrochloride, indomethacin, pentazocine, acetylcholine chloride, alimemazine tartrate, cyproheptadine hydrochloride, diphenhydramine hydrochloride, chlorpheniramine maleate, codeine phosphate, dihydrocodeine phosphate, dextromethorphan hydrobromide, pentoxyverine citrate, theophylline, aminophylline, ephedrine hydrochloride, epinephrine hydrochloride, salbutamol sulfate, trimetoquinol hydrochloride, procaterol hydrochloride, methylephedrine hydrochloride, phenylpropanolamine hydrochloride, guaifenesin, tranexamic acid, anhydrous caffeine, caffeine, choline salicylate and sodium salicylate. The drug may be used singly or in combination of two or more.

The core particle containing a drug may be a drug substance, a granule prepared by wet granulation, dry granulation or another granulation, or a layering particle prepared by layering of a drug around a core of crystalline cellulose, mannitol, lactose or the like. When the core particle containing a drug is produced by granulation or layering, a various additive commonly usable in the field, such as an excipient, a binder or a disintegrant, can be blended.

The amount of the coating composition applied onto the surface of the core particle containing a drug varies depending on the shape and size of the drug substance or the particle containing a drug, the properties of the drug and the additive contained by the particle, and the like. An approximate total coating amount is preferably 1 to 500 parts by weight, more preferably 5 to 100 parts by weight, even more preferably 10 to 50 parts by weight relative to 100 parts by weight of the particle containing a drug.

The solid preparation obtained by coating of the coating composition has an average particle size of preferably 300 μm or less, more preferably 20 to 270 μm or less, even more preferably 50 to 250 μm or less from the standpoint of the avoidance of unpleasant granular texture in the oral cavity. The average particle size is an average particle size in terms of volume, and is determined in accordance with a powdery particle size measurement method by laser diffractometry. For example, a HELOS & RODOS (manufactured by Japan Laser Corporation) can be used for the measurement.

The coating apparatus is not particularly limited. Examples of the coating apparatus include a pan coating apparatus, a fluidized bed coating apparatus, a tumbling fluidized bed coating apparatus, a Wurster fluidized bed and a composite fluidized bed. A special coating apparatus such as the Wurster fluidized bed and the composite fluidized bed is conventionally required for fine particle coating, but the coating composition in the present invention has low adhesiveness so that it is so advantageous as to allow coating even with a common fluidized bed coating apparatus to be carried out.

EXAMPLES

The present invention will be described further in detail with reference to Examples and Comparative Examples. However, it should not be construed that the invention is limited to or by Examples.

Synthesis Example 1

A wood pulp having an intrinsic viscosity of 1,400 ml/g was pulverized with a pulverizer to obtain a cellulose pulp powder. Of the cellulose pulp powder, the cellulose pulp powder in an amount corresponding to 6.0 kg of cellulose was placed in an internal-stirring pressure-resistant reactor with a jacket. The reactor was vacuumed and purged with nitrogen to remove oxygen thoroughly from the reactor. Next, the inside temperature of the reactor was adjusted to 55° C. with stirring of the inside thereof, and a 49% by weight aqueous sodium hydroxide solution was added thereto as a first alkali metal hydroxide solution at an addition rate of 12.04 [mol/mol·hr] in such an amount that a molar ratio of the first sodium hydroxide to the cellulose (first sodium hydroxide/cellulose) became 3.01, to obtain alkali cellulose.

Then 2.4 kg of dimethyl ether was added to the reactor, and the inside temperature of the reactor was controlled to maintain the inside temperature at 60° C. After the addition of dimethyl ether, the inside temperature of the reactor was increased from 60° C. to 80° C., while adding methyl chloride to the reactor over 60 minutes in such an amount that a molar ratio of the methyl chloride to the total amount of the first and second sodium hydroxides (methyl chloride/total sodium hydroxide) became 1.1, to obtain a first reaction mixture. Subsequently to the addition of methyl chloride, a 49% by weight aqueous sodium hydroxide solution was added as a second alkali metal hydroxide solution at an addition rate of 2.58 [mol/mol·hr] in such an amount that a molar ratio of the second sodium hydroxide to the cellulose (second sodium hydroxide/cellulose) became 1.26, to obtain a second reaction mixture. The inside temperature of the reactor was 81° C. at the start of the addition of the second sodium hydroxide solution, and 89° C. at the completion of the addition, while increasing the inside temperature of the reactor at an increase rate of 16.4° C./hr from the start to the completion of the addition of the second aqueous sodium hydroxide solution. After the completion of the addition of the second aqueous sodium hydroxide solution, the stirring was continued for 30 minutes to complete the etherification. The ratio of the weight of the first sodium hydroxide in the first aqueous sodium hydroxide solution to the total weight of the first and second sodium hydroxides in the first and second aqueous sodium hydroxide solutions was 70.5% by weight.

The obtained second reaction mixture was subjected to addition of hot water of 95° C. to become a slurry, then washed by using a rotary pressure filter, dried with an air dryer, and pulverized with a ball mill to obtain methyl cellulose.

The obtained methyl cellulose was subjected to addition of a 10% by weight aqueous hydrochloric acid solution in such an amount that the hydrochloric acid content became 0.3% by weight relative to the amount of the methyl cellulose. The depolymerization was carried out for 90 minutes while adjusting the inside temperature of the reactor to 82° C., to obtain low-polymerization-degree methyl cellulose. The low-polymerization-degree methyl cellulose was pulverized with a high speed rotary impact grinder, Victory Mill, having a screen with a mesh size of 0.3 mm, to obtain intended low-polymerization-degree methyl cellulose. The degree of substitution of methoxy group of the obtained low-polymerization-degree methyl cellulose, the viscosity at 20° C. of a 2% by weight aqueous solution thereof, the dissolution start temperature of 12% by weight dispersion thereof, and the gelation temperature of a 15% by weight aqueous solution thereof are shown in Table 1.

Synthesis Example 2

In the same manner as in Synthesis Example 1, a cellulose pulp was placed in a reactor. The inside temperature of the reactor was adjusted to 55° C. with stirring of the inside thereof, and a 49% by weight aqueous sodium hydroxide solution was added thereto as a first alkali metal hydroxide solution at an addition rate of 11.39 [mol/mol·hr] in such an amount that a molar ratio of the first sodium hydroxide to the cellulose (first sodium hydroxide/cellulose) became 2.85, to obtain alkali cellulose.

Then the same procedure as in Synthesis Example 1 was carried out to obtain a first reaction mixture. Next, the same procedure as in Synthesis Example 1 was carried out to obtain a second reaction mixture except that the inside temperature of the reactor was 79° C. at the start of the addition of the second aqueous sodium hydroxide solution, and 91° C. at the completion of the addition, while increasing the inside temperature of the reactor at an increase rate of 24° C./hr from the start of the addition of the second aqueous sodium hydroxide solution to the completion of the addition; and the second aqueous sodium hydroxide solution was added at an addition rate of 2.80 [mol/mol·hr] in such an amount that a molar ratio of the second sodium hydroxide to the cellulose (second sodium hydroxide/cellulose) became 1.40. The ratio of the weight of the first sodium hydroxide in the first aqueous sodium hydroxide solution to the total weight of the first and second sodium hydroxides in the first and second aqueous sodium hydroxide solutions was 67.0% by weight.

The obtained second reaction mixture was then purified and pulverized in the same manner as in Synthesis Example 1 to isolate methyl cellulose. The methyl cellulose had a degree of substitution (DS) of methoxy group of 1.82.

The obtained methyl cellulose was subjected to addition of a 10% by weight aqueous hydrochloric acid solution in such an amount that the hydrochloric acid content became 0.3% by weight relative to the amount of the methyl cellulose. The depolymerization was carried out for 90 minutes while adjusting the inside temperature of the reactor to 82° C., to obtain low-polymerization-degree methyl cellulose. Physical properties of the obtained low-polymerization-degree methyl cellulose are shown in Table 1.

Synthesis Example 3

In the same manner as in Synthesis Example 1, a cellulose pulp was placed in a reactor. The inside temperature of the reactor was adjusted to 60° C. with stirring of the inside thereof, and a 49% by weight aqueous sodium hydroxide solution was added thereto as a first alkali metal hydroxide solution at an addition rate of 10.48 [mol/mol·hr] in such an amount that a molar ratio of the first sodium hydroxide to the cellulose (first sodium hydroxide/cellulose) became 2.62, to obtain alkali cellulose.

Then the same procedure as in Synthesis Example 1 was carried out to obtain a first reaction mixture. Next, the same procedure as in Synthesis Example 1 was carried out to obtain a second reaction mixture except that the inside temperature of the reactor was 77° C. at the start of the addition of the second aqueous sodium hydroxide solution, and 89° C. at the completion of the addition, while increasing the inside temperature of the reactor at an increase rate of 24° C./hr from the start of the addition of the second aqueous sodium hydroxide solution to the completion of the addition, and the second aqueous sodium hydroxide solution was added at an addition rate of 3.20 [mol/mol·hr] in such an amount that a molar ratio of the second sodium hydroxide to the cellulose (second sodium hydroxide/cellulose) became 1.60. The ratio of the weight of the first sodium hydroxide in the first aqueous sodium hydroxide solution to the total weight of the first and second sodium hydroxides in the first and second aqueous sodium hydroxide solutions was 62.1% by weight.

The obtained second reaction mixture was then purified and pulverized in the same manner as in Synthesis Example 1 to isolate methyl cellulose. The methyl cellulose had a degree of substitution (DS) of methoxy group of 1.81.

The obtained methyl cellulose was subjected to addition of a 10% by weight aqueous hydrochloric acid solution in such an amount that the hydrochloric acid content became 0.3% by weight relative to the amount of the methyl cellulose. The depolymerization was carried out for 90 minutes while adjusting the inside temperature of the reactor to 82° C., to obtain low-polymerization-degree methyl cellulose. Physical properties of the obtained low-polymerization-degree methyl cellulose are shown in Table 1.

Comparative Synthesis Example 1

In the same manner as in Synthesis Example 1, a cellulose pulp was placed in a reactor. The inside temperature of the reactor was adjusted to 60° C. with stirring of the inside thereof, and a 49% by weight aqueous sodium hydroxide solution was added thereto at an addition rate of 18.88 [mol/mol·hr] in such an amount that a molar ratio of the sodium hydroxide to the cellulose became 4.72, to obtain alkali cellulose. Contrary to Synthesis Examples 1 and 2, the aqueous sodium hydroxide solution was added in one step.

Then 2.4 kg of dimethyl ether was added to the reactor, and the inside temperature of the reactor was controlled to maintain the inside temperature at 60° C. After the addition of dimethyl ether, the inside temperature of the reactor was increased from 60° C. to 80° C., while adding methyl chloride to the reactor over 60 minutes in such an amount that a molar ratio of the methyl chloride to sodium hydroxide (methyl chloride/sodium hydroxide) became 1.1. The etherification was carried out for 70 minutes while increasing the inside temperature of the reactor from 80° C. to 95° C. after the addition of methyl chloride, to obtain crude methyl cellulose. The stirring was continued for 60 minutes to complete the etherification.

The obtained reaction mixture containing the crude methyl cellulose was subjected to addition of hot water to become a slurry, then washed by using a rotary pressure filter, dried with an air dryer, and pulverized with a ball mill to obtain methyl cellulose.

The obtained methyl cellulose was subjected to addition of a 10% by weight aqueous hydrochloric acid solution in such an amount that the hydrochloric acid content became 0.3% by weight relative to the amount of the methyl cellulose. The depolymerization was carried out for 70 minutes while adjusting the inside temperature of the reactor to 80° C., to obtain low-polymerization-degree methyl cellulose. The low-polymerization-degree methyl cellulose was pulverized with a high speed rotary impact grinder, Victory Mill, having a screen with a mesh size of 0.3 mm, to obtain intended low-polymerization-degree methyl cellulose. Physical properties of the obtained low-polymerization-degree methyl cellulose are shown in Table 1.

Comparative Synthesis Example 2

In the same manner as in Synthesis Example 1, a cellulose pulp was placed in a reactor. The inside temperature of the reactor was adjusted to 60° C. with stirring of the inside thereof, and a 49% by weight aqueous sodium hydroxide solution was added thereto at an addition rate of 20.24 [mol/mol·hr] in such an amount that a molar ratio of the sodium hydroxide to the cellulose became 5.06, to obtain alkali cellulose.

Then 2.4 kg of dimethyl ether was added to the reactor, and the inside temperature of the reactor was controlled to maintain the inside temperature at 60° C. After the addition of dimethyl ether, the inside temperature of the reactor was increased from 60° C. to 80° C., while adding 2.79 kg of propylene oxide over 10 minutes, and then adding methyl chloride over 60 minutes in such an amount that a molar ratio of the methyl chloride to the sodium hydroxide (methyl chloride/sodium hydroxide) became 1.1, for the etherification reaction. The stirring was continued for 60 minutes, while gradually increasing the inside temperature of the reactor from 80° C. to 95° C., to complete the etherification.

The obtained reaction mixture was subjected to addition of hot water to become a slurry, then washed with a rotary pressure filter, dried with an air dryer, and pulverized with a ball mill to obtain hypromellose. Physical properties of the obtained hypromellose are shown in Table 1.

TABLE 1

| | addition of NaOH | ratio of first NaOH (%) *1 | degree of substitution of methoxy (DS) | degree of substitution of hydroxypropoxy (MS) | viscosity of 2 wt % aq. solution (mPa·s) | dissolution start temp. (° C.) | gelation temp. (° C.) |
|---|---|---|---|---|---|---|---|
| Syn. Ex. 1 | 2 steps | 70.5 | 1.85 | — | 4.2 | 22.4 | 22.4 |
| Syn. Ex. 2 | 2 steps | 67.0 | 1.85 | — | 4.2 | 20.2 | 19.5 |
| Syn. Ex. 3 | 2 steps | 62.1 | 1.85 | — | 4.2 | 16.4 | 15.1 |
| Comp. Syn. Ex. 1 | 1 step | — | 1.85 | — | 4.1 | 30.1 | 29.5 |
| Comp. Syn. Ex. 2 | 1 step | — | 1.89 | 0.24 | 4.5 | 54.1 | 50.2 |

*1 It means the ratio of the weight of the first NaOH to the total weight of the first and second NaOH.

As compared with Comparative Synthesis Examples 1 and 2 in which typical production methods of methyl celluloses were carried out, Synthesis Examples 1 to 3 resulted in lower dissolution start temperatures and lower gelation temperatures.

Example 1

The 47.5 g of water of 20° C. and 2.5 g of the methyl cellulose obtained in Synthesis Example 1 were placed in a 100-mL beaker, and stirred with a stirring propeller at 300 rpm for 5 minutes to obtain a coating composition. The coating composition was sieved through a sieve having a mesh size of 350 μm. The agglomerates on the sieve were collected, and dried at 80° C. for twenty-four hours. The weight of agglomerates after drying was measured, and the undissolved residual ratio was calculated in accordance with the following equation. The result is shown in Table 2.

Undissolved residual ratio (%)=(weight of agglomerates after drying/weight of sample)×100

Example 2

The same procedure as in Example 1 was carried out to obtain the undissolved residual ratio except that the methyl cellulose obtained in Synthesis Example 2 was used in the place of the methyl cellulose obtained in Synthesis Example 1. The result is shown in Table 2.

Example 3

The same procedure as in Example 1 was carried out to obtain the undissolved residual ratio except that the methyl cellulose obtained in Synthesis Example 3 was used in the place of the methyl cellulose obtained in Synthesis Example 1. The result is shown in Table 2.

Comparative Example 1

The same procedure as in Example 1 was carried out to obtain the undissolved residual ratio except that the methyl cellulose obtained in Comparative Synthesis Example 1 was used in the place of the methyl cellulose obtained in Synthesis Example 1. The result is shown in Table 2.

Comparative Example 2

The same procedure as in Example 1 was carried out to obtain the undissolved residual ratio except that the hypromellose obtained in Comparative Synthesis Example 2 was used in the place of the methyl cellulose obtained in Synthesis Example 1. The result is shown in Table 2.

TABLE 2

|  | kind of cellulose ether | undissolved residual ratio (%) |
|---|---|---|
| Example 1 | methyl cellulose obtained in Syn. Ex. 1 | 0.4 |
| Example 2 | methyl cellulose obtained in Syn. Ex. 2 | 0.2 |
| Example 3 | methyl cellulose obtained in Syn. Ex. 3 | 0.1 |
| Comp. Ex. 1 | methyl cellulose obtained in Comp. Syn. Ex. 1 | 14.0 |
| Comp. Ex. 2 | hypromellose obtained in Comp. Syn. Ex. 2 | 60.8 |

In Comparative Examples 1 and 2, the methyl cellulose obtained in Comparative Synthesis Example 1 and the hypromellose obtained in Comparative Synthesis Example 2 had higher dissolution start temperatures than normal temperature, so that when the methyl cellulose and the hypromellose was added to water of normal temperature, only the surfaces thereof was dissolved to form agglomerates (mamako in Japanese) and large amounts of undissolved residues were observed. On the other hand, in Examples 1 to 3, the methyl celluloses obtained in Synthesis Examples 1 to 3 had dissolution start temperatures within a normal temperature range, so that they were immediately moistened and dissolved to leave small amounts of undissolved residues, and as a result, the coating compositions could be produced at normal temperature.

Example 4

(Coating)
The methyl cellulose and polyethylene glycol 6000 shown below were directly dissolved in water at normal temperature to obtain a coating composition. The methyl cellulose was immediately dissolved, and no agglomerates were observed.

| methyl cellulose obtained in Synthesis Example 1 | 150 g (7.0 parts by weight) |
|---|---|
| polyethylene glycol 6000 | 75 g (3.5 parts by weight) |
| purified water | 1,918 g (89.5 parts by weight) |

The 500 g of acetaminophen crystal type S having an average particle size of 198 μm was placed in a fluidized bed coating apparatus, Multiplex MP-01 manufactured by Powrex Corp., and was subjected to coating by the coating composition in a top spray manner in conditions of an intake air temperature of 75° C., an exhaust air temperature of 40 to 42° C., a fluidized air amount of 1.2 $m^3$/min, a spray air pressure of 200 kPa and a spray air amount of 35 L/min. The coating was performed to 30% by weight in terms of methyl cellulose.

(Lump Ratio)
The obtained coated granules were sieved through a sieve with a mesh size of 710 μm, and the lump ratio was determined from the weight on the sieve to the total weight of the coated granules. The result is shown in Table 3.

(Product Yield)
The recovery amount of the coated granules sieved through a sieve with a mesh size of 710 μm was measured, and the product yield was determined based on a theoretical recovery amount calculated from the used methyl cellulose. The result is shown in Table 3.

(Dissolution Test)
The coated granules was subjected to the dissolution test in accordance with Dissolution Test, Paddle method in the Japanese Pharmacopoeia Sixteenth Edition at a paddle rotation rate of 100 rpm with water as the test liquid, and the drug concentration was quantitatively determined at a measurement wavelength of 244 nm by using an ultraviolet spectrophotometer (UV-1700, manufactured by Shimadzu Corporation). The dissolution rates after 1 minute and 10 minutes are shown in Table 3.

As Reference Example 1, the dissolution rates of an acetaminophen powder after 1 minute and 10 minutes are also shown in Table 3.

(Sensory Test)
The coated granules were taken by six volunteers at the amount of 50 mg per volunteer. The granules were slowly moved in the oral cavity, and the time until bitterness was sensed was measured. The average time was calculated. The result is shown in Table 3.

Example 5

Coating was carried out in the same manner as in Example 4 except that the methyl cellulose produced in Synthesis Example 2 was used. The results are shown in Table 3.

Example 6

Coating was carried out in the same manner as in Example 4 except that the methyl cellulose produced in Synthesis Example 3 was used. The results are shown in Table 3.

Comparative Example 3

Coating was carried out in the same manner as in Example 4 except that the methyl cellulose produced in Comparative Synthesis Example 1 was used. The results are shown in Table 3.

Comparative Example 4

Coating was carried out in the same manner as in Example 4 except that the hypromellose produced in Comparative Synthesis Example 2 was used. The results are shown in Table 3.

Reference Example 1

As a control, the dissolution rate after 1 minute, the dissolution rate after 10 minutes, and the sensory test result of acetaminophen crystal type S having an average particle size of 198 μm before coating are shown in Table 3.

TABLE 3

|  | kind of cellulose ether | lump ratio (%) | product yield (%) | dissolution ratio after 1 minute (%) | dissolution ratio after 10 minutes (%) | time until bitterness was sensed (sec) |
|---|---|---|---|---|---|---|
| Example 4 | MC obtained in Syn. Ex. 1 | 0.83 | 95.3 | 4.1 | 99.1 | 25 |
| Example 5 | MC obtained in Syn. Ex. 2 | 0.65 | 95.4 | 3.1 | 99.3 | 28 |
| Example 6 | MC obtained in Syn. Ex. 3 | 0.56 | 95.5 | 2.0 | 99.0 | 31 |
| Comp. Ex. 3 | MC obtained in Comp. Ex. 1 | 18.8 | 73.2 | 8.0 | 99.6 | 10 |
| Comp. Ex. 4 | HPMC obtained in Comp. Ex. 2 | 37.4 | 55.2 | 15.6 | 99.7 | 3 |
| Ref. Ex. 1 | — | — | — | 48.0 | 99.6 | 1 |

* MC is an abbreviation of methyl cellulose and HPMC is an abbreviation of hypromellose.

In Examples 4 to 6, the tackiness was reduced during the coating due to a low gelation temperature, and substantially no lumps were formed even for the coating of fine particle. As for the dissolution characteristics, the initial dissolution after 1 minute was suppressed, and the dissolution after 10 minutes was excellent. Also in the sensory test, the bitterness masking effect was high.

The invention claimed is:

1. A coating composition comprising:
   methyl cellulose having a viscosity that a viscosity at 20° C. is 1 to 15 mPa s, as determined in a 2% by weight aqueous solution of the methyl cellulose in water, and a dissolution start temperature of 10 to 25° C., as determined in a 12% by weight aqueous dispersion of the methyl cellulose in water; and
   a solvent.

2. The coating composition according to claim 1, wherein a 15% by weight aqueous solution of the methyl cellulose has a gelation temperature of 13 to 25° C.

3. The coating composition according to claim 1, wherein the solvent is water or a mixed solvent of water and an alcohol.

4. The coating composition according to claim 2, wherein the solvent is water or a mixed solvent of water and an alcohol.

5. A solid preparation comprising a drug substance or a core particle containing a drug, and a coating comprising the coating composition according to claim 1.

6. A solid preparation comprising a drug substance or a core particle containing a drug, and a coating comprising the coating composition according to claim 2.

7. A solid preparation comprising a drug substance or a core particle containing a drug, and a coating comprising the coating composition according to claim 3.

8. The solid preparation according to claim 5, wherein the solid preparation has an average particle size of 300 mm or less.

9. A method for producing a coating composition, the method comprising the steps of:
   mixing a cellulose pulp and a first alkali metal hydroxide solution with stirring to obtain alkali cellulose;
   reacting the alkali cellulose with a methylating agent to obtain a first reaction mixture;
   mixing the first reaction mixture and a second alkali metal hydroxide solution with stirring and without further addition of any methylating agent to obtain a second reaction mixture;
   isolating methyl cellulose from the second reaction mixture;
   depolymerizing the methyl cellulose to obtain a depolymerized methyl cellulose; and
   dissolving the depolymerized methyl cellulose in a solvent, wherein a ratio of a weight of a first alkali metal hydroxide in the first alkali metal hydroxide solution to a total weight of the first alkali metal hydroxide in the first alkali metal hydroxide solution and a second alkali metal hydroxide in the second alkali metal hydroxide solution is 50 to 86%.

* * * * *